United States Patent [19]

Wahle et al.

[11] Patent Number: 5,783,534
[45] Date of Patent: Jul. 21, 1998

[54] PROCESS FOR THE PRODUCTION OF SOLID ESTERQUATS

[75] Inventors: Bernd Wahle, Kaarst, Germany; Joaquim Bigorra Llosas, Sabadell, Spain; Rafael Pi, Granollers, Spain; Antoni Soler Codina, Terassa, Spain; Emili Brau Balague, Santa Barbara, Spain; Yvonne Reichert, Krefeld, Germany; Peter Waltenberger, Breitscheid, Germany

[73] Assignee: Henkel Kommanditgesellschaft auf Aktien, Duesseldorf, Germany

[21] Appl. No.: 648,100

[22] PCT Filed: Nov. 11, 1994

[86] PCT No.: PCT/EP94/03743

§ 371 Date: Jul. 15, 1996

§ 102(e) Date: Jul. 15, 1996

[87] PCT Pub. No.: WO95/14654

PCT Pub. Date: Jun. 1, 1995

[30] Foreign Application Priority Data

Nov. 20, 1993 [DE] Germany ............... 43 39 643.7

[51] Int. Cl.$^6$ ............... A61K 7/075; Z07C 219/02; C07C 209/00
[52] U.S. Cl. ............... 510/124; 510/125; 510/499; 510/504; 510/515; 424/70.28; 554/85; 554/109; 554/110; 554/114; 558/27; 564/281; 564/285; 564/292; 564/294; 564/296
[58] Field of Search ............... 510/124, 125, 510/515, 535, 499, 504; 424/70.28; 554/85, 109, 110, 114; 558/27; 564/281, 285, 292, 294, 296

[56] References Cited

U.S. PATENT DOCUMENTS

| | | | |
|---|---|---|---|
| 3,915,867 | 10/1975 | Kang et al. | 252/8.8 |
| 4,370,272 | 1/1983 | Wechsler et al. | 260/404 |
| 5,443,631 | 8/1995 | Brock et al. | 106/244 |
| 5,463,094 | 10/1995 | Brown et al. | 554/110 |
| 5,482,636 | 1/1996 | Brock et al. | 252/8.8 |

FOREIGN PATENT DOCUMENTS

| | | |
|---|---|---|
| 008 839 | 3/1980 | European Pat. Off. . |
| 239 910 | 10/1987 | European Pat. Off. . |
| 284 036 | 9/1988 | European Pat. Off. . |
| 293 955 | 12/1988 | European Pat. Off. . |
| 295 739 | 12/1988 | European Pat. Off. . |
| 309 052 | 3/1989 | European Pat. Off. . |
| 569 847 | 11/1993 | European Pat. Off. . |
| 604 726 | 7/1994 | European Pat. Off. . |
| WO 91/01295 | 2/1991 | WIPO . |

OTHER PUBLICATIONS

O. Ponsati, C.R. CED–Congress, Barcelona, 167 (1992), pp. 167–179.

R. Puchta, C.R. CED–Congress, Sitges, 59 (1993) pp. 59–68.

*Primary Examiner*—Anthony Green
*Attorney, Agent, or Firm*—Ernest G. Szoke; Wayne C. Jaeschke; Henry E. Millson, Jr.

[57] ABSTRACT

A process for the production of a solid esterquat free from solvents comprising the steps of A) forming a mixture comprising (i) at least one fatty acid triethanolamine ester corresponding to formula (I)

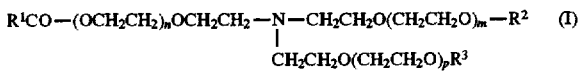

in which $R^1CO$ is a saturated and/or unsaturated acyl radical containing 6 to 22 carbon atoms, $R^2$ and $R^3$ independently of one another represent hydrogen or have the same meaning as $R^1CO$, and n, m and p together stand for 0 or for a number of from 1 to 10;

(ii) at least one fatty alcohol polyglycol ether, and (iii) at least one fatty acid partial glyceride; and B) adding an alkylating agent to the above mixture to form said solid esterquat.

19 Claims, No Drawings

PROCESS FOR THE PRODUCTION OF SOLID ESTERQUATS

BACKGROUND OF THE INVENTION

1. Field of the Invention

This invention relates to solid esterquats which are obtained by quaternizing fatty acid triethanolamine esters in the presence of selected dispersants and to the use of the esterquats mentioned for the production of surface-active formulations.

Statement of Related Art

2. Prior Art

Various compounds or mixtures of compounds are used for the treatment of textile fibers, yarns or fabrics. They provide the textiles thus treated with the required properties or are constituents of fabric care formulations. The processing properties of the textiles, their wear properties and also their care can be improved according to the type of active substances used.

Products essentially containing quaternized ester salts of fatty acids with alkanolamines, so-called "esterquats", have acquired significance in recent years in the field of textile treatment compositions. U.S. Pat. No. 3,915,867, U.S. Pat. No. 4,370,272, EP 0 239 910 A2, EP 0 293 955 A2, EP 0 295 739 A2 and EP 0 309 052 A2 are cited as representative of the extensive literature available on this subject.

Esterquats are not only distinguished by excellent softening and antistatic properties, they also show surprisingly high biological degradability for cationic surfactants. Unfortunately, the disadvantage of esterquats is that they are normally marketed in the form of aqueous dispersions which do not always show satisfactory stability in storage. Thus, they are often observed to undergo unfavorable changes in viscosity, phase separation or sedimentation. Another disadvantage of esterquats is that they are normally formulated as alcohol-based concentrates which have to be diluted with water to the in-use concentration. In this respect, too, there is a need for products which are free from solvents.

Accordingly, the problem addressed by the present invention was to provide a process for the solventless production of solid esterquats which would form stable aqueous dispersions of consistently favorable viscosity.

DESCRIPTION OF THE INVENTION

The present invention relates to a process for the production of solid esterquats, in which fatty acid triethanolamine esters corresponding to formula (I):

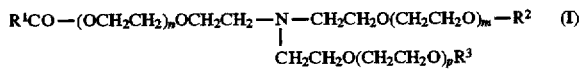

in which $R^1CO$ is a saturated and/or unsaturated acyl radical containing 6 to 22 carbon atoms, $R^2$ and $R^3$ independently of one another represent hydrogen or have the same meaning as $R^1CO$ and n, m and p together stand for 0 or for numbers of 1 to 10, are quaternized in known manner with alkylating agents in the presence of a) fatty alcohol polyglycol ethers and
b) fatty acid partial glycerides.

It has surprisingly been found that the quaternization of fatty acid triethanolamine esters can also be carried out in the presence of the dispersants mentioned. Solvent-free, more especially alcohol-free, solid esterquats are obtained in this way and form dispersions that are stable in two respects: on the one hand, neither phase separation nor sedimentation occurs, even in the event of prolonged storage; on the other hand, the dispersions have a constant viscosity. The invention includes the observation that the subsequent addition of the dispersants mentioned to conventionally prepared esterquats only improves dispersibility very slightly, if at all.

Esterquats and fatty acid triethanolamine esters

Esterquats are a known group of cationic surfactants which are normally obtained by esterification of triethanolamine or triethanolamine polyglycol ethers with fatty acids and subsequent quaternization in organic solvents. The production and properties of esterquats are described, for example, in WO 91/01295 (Henkel) and in the synoptic articles by O. Ponsati in C.R. CED-Congress, Barcelona, 167 (1992) and by R. Puchta in C.R. CED-Congress, Sitges, 59 (1993).

Suitable starting materials for the production of the esterquats by the process according to the invention are fatty acid triethanolamine esters corresponding to formula (I) which preferably represent technical monoester/diester/triester mixtures in which the degree of esterification is between 1.2 and 2.5 and more particularly between 1.5 and 1.9. Particularly preferred esters are derived from technical $C_{12/18}$ or $C_{16/18}$ fatty acids, for example palm oil fatty acid, coconut oil fatty acid or tallow fatty acid, and may have an iodine value of 0 to 40.

Dispersants

Fatty alcohol polyglycol ethers corresponding to formula (II):

in which $R^4$ is a linear or branched aliphatic hydrocarbon radical containing 6 to 22 carbon atoms and 0 and/or 1, 2 or 3 double bonds and q is a number of 10 to 50, are suitable as a first dispersant component.

These substances are known nonionic surfactants which are industrially produced by base-catalyzed addition of ethylene oxide onto fatty alcohols. Typical examples are adducts of 10 to 50 moles, preferably 25 to 45 moles and more preferably 30 to 40 moles of ethylene oxide with caproic alcohol, caprylic alcohol, 2-ethylhexyl alcohol, capric alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, and erucyl alcohol and the technical mixtures thereof which may be obtained, for example, by high-pressure hydrogenation of native fatty acid methyl ester fractions or aldehydes from Roelen's oxosynthesis. Adducts of, on average, 30 to 40 moles of ethylene oxide with technical $C_{12/18}$ cocoalcohol or $C_{16/18}$ tallow alcohol cuts are preferably used.

The second dispersant component may be selected from fatty acid partial glycerides which are preferably technical mixtures of monoesters and/or diesters of glycerol with fatty acids corresponding to formula (III):

in which $R^5CO$ is an aliphatic acyl radical containing 6 to 22 carbon atoms. Typical examples are monoglyceride and/or diglyceride mixtures based on caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of fats and oils. Monoglycerides of lauric acid, palmitic acid, stearic acid, oleic acid and $C_{12/18}$ cocofatty acid and $C_{16/18}$ tallow fatty acid are preferably used.

Aqueous dispersions with particularly favorable stability are obtained by using solid esterquats which have been produced using the fatty acid triethanolamine esters, the fatty alcohol polyglycol ethers and the fatty acid partial glycerides in a ratio by weight of (40 to 60):(10 to 25):(15 to 50) and preferably in a ratio by weight of (44.5 to 51.0):(16.0 to 18.0):(32.5 to 39.0), with the proviso that the figures add up to 100 parts by weight.

Alkylation

The alkylation of the fatty acid triethanolamine esters may be carried out in known manner. To this end, the ester is initially introduced together with the dispersant mixture and the resulting mixture is stirred with the alkylating agent (which is normally used in equimolar quantities or in a slight excess) at elevated temperatures. On completion of the reaction, unreacted alkylating agent may be destroyed by addition of a small quantity of amino acid, preferably glycine. Suitable alkylating agents are alkyl halides, dialkyl sulfates and ethylene oxide—the latter in the presence of dialkyl phosphates. The process according to the invention is preferably used for the production of methyl-quaternized esterquats in the form of their chlorides or methyl sulfate salts and esterquat salts which have been quaternized with 1 to 5 moles of ethylene oxide.

Commercial Applications

The esterquats obtainable by the process according to the invention are readily dispersible in water. The resulting dispersions have a constant viscosity, even in the event of prolonged storage, and do not show any tendency towards phase separation or sedimentation. Materials which have been treated with the esterquats produced by the process according to the invention are distinguished by increased rewetting power.

Accordingly, the present invention also relates to the use of the esterquats obtainable by the process according to the invention for the production of surface-active formulations, more especially fabric softeners and conditioners and hair care formulations in which they may be present in quantities of 10 to 100% by weight and preferably in quantities of 20 to 60% by weight, based on the solids content of the formulation. Hair care formulations in the context of the invention are, for example, hair shampoos, hair rinses, hair setting formulations, blow-dry formulations and the like. The formulations preferably have a pH value of 3 to 5 and more preferably 3 to 4.

The following Examples are intended to illustrate the invention without limiting it in any way.

EXAMPLES

I. Preparation of the esterquats

Example 1 a) Esterification. 324 g (1.2 moles) of partly hydrogenated $C_{16/18}$ tallow fatty acid (iodine value 40), 149 g (1 mole) of triethanolamine and 1.4 g of 50% by weight hypophosphorous acid were introduced into a 1 liter three-necked flask equipped with a stirrer, internal thermometer and distillation head.

The reaction mixture was heated to a temperature of 160° C. over a period of 4 h under a reduced pressure of 40 mbar until the acid value was below 5. The crude tallow fatty acid triethanolamine ester was then cooled, the reaction mixture was vented and 1 liter of air was passed through for 15 minutes with continuous stirring.

b) Quaternization. A mixture consisting of b1) 69.2 g (0.153 mole) corresponding to 44.5% by weight of the ester from 1a), b2) 25.6 g (0.012 mole) corresponding to 16.5% by weight of $C_{16/18}$ tallow fatty alcohol 40 EO and b3) 60.7 g (0.169 mole) corresponding to 39.0% by weight of glycerol monostearate (Monomuls® 90S18, CF Grünau, Illertissen, FRG)

was introduced into a 500 ml three-necked flask equipped with a stirrer, dropping funnel and reflux condenser and heated with stirring to 45° C.

18.9 g (0.15 mole) of dimethyl sulfate was added dropwise over a period of 2 h. After the addition, the mixture was stirred for another 2 h at 60° C. and unreacted DMS was destroyed by addition of 0.4 g (0.005 mole) of glycine. The water-free esterquat/emulsifier mixtures were obtained in the form of light-colored wax-like compounds which were optionally mechanically flaked in a subsequent step.

Example 2

The procedure was as in Example 1, except that the quaternization was carried out with a mixture having the following composition:

b1) 89.3 g (0.197 mole) corresponding to 57.5% by weight of the ester from a), b2) 15.5 g (0.007 mole) corresponding to 10.0% by weight of $C_{16/18}$ tallow alcohol 40 EO and b3) 50.4 g (0.141 mole) corresponding to 32.5% by weight of glycerol monostearate.

Example 3

The procedure was as in Example 1, except that the quaternization was carried out with a mixture having the following composition:

b1) 73.4 g (0.159 mole) corresponding to 46.7% by weight of the ester from a), b2) 49.3 g (0.021 mole) corresponding to 31.7% by weight of $C_{16/18}$ tallow alcohol 40 EO and b3) 33.4 g (0.09 mole) corresponding to 21.6% by weight of glycerol monostearate.

II. Application Examples

Quantities of 10 g of the water-free solid esterquats from I) were dissolved in 90 g of water and the pH value of the resulting solutions was adjusted to 3.3. The dispersions were formed by gentle stirring at room temperature. Homogeneous dispersions were obtained in every case. The viscosity of the dispersions was determined after storage for 1, 2 and 15 d (Brookfield RVT, spindle 2, 25° C., 20 r.p.m.) while their stability was visually evaluated after 15 d. The results are set out in Table 1 below.

TABLE 1

| | | Viscosity measurements | | | |
|---|---|---|---|---|---|
| | Production | Viscosity (mPas) | | | Stability |
| Example | Example | 1 d | 2 d | 15 d | 15 d |
| 4 | 1 | 100 | 98 | 98 | +++ |
| 5 | 2 | 100 | 98 | 98 | +++ |
| 6 | 3 | 100 | 98 | 98 | +++ |

+++) = No phase separation, no sedimentation

Comparison tests

For comparison, a commercially available esterquat (Dehyquart® AU 46, 90% by weight solution in isopropyl alcohol, a product of Pulcra S. A., Barcelona, Spain) was first freed from the solvent and then, i.e. subsequently, mixed with the dispersants mentioned in the quantity ratios indicated. In all the comparison tests, it was found that distinctly more intensive shearing was necessary to form the dispersion. Although similar initial values were obtained in regard to the viscosity of the comparison dispersions, a rapid reduction in viscosity was observed after brief storage. In addition, the comparison dispersions showed poorer stability in storage.

We claim:

1. A process for the production of a solid esterquat free from solvents comprising the steps of
A) forming a mixture comprising
   (i) at least one fatty acid triethanolamine ester of formula (I)

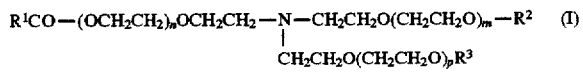

in which $R^1CO$ is a saturated and/or unsaturated acyl radical containing 6 to 22 carbon atoms, $R^2$ and $R^3$ independently of one another represent hydrogen or have the same meaning as $R^1CO$, and n, m and p together stand for O or for a number of from 1 to 10;
   (ii) at least one fatty alcohol polyglycol ether, and
   (iii) at least one fatty acid partial glyceride; and
B) adding an alkylating agent to the above mixture to form said solid esterquat; wherein in step A) components (i), (ii), and (iii) are present in a ratio by weight of about (40 to 60):(10 to 25):(15 to 50), with the proviso that these numbers add up to 1 00 parts by weight.

2. The process of claim 1 wherein in step A), component (ii) is at least one fatty alcohol polyglycol ether of formula (II):

$$R^4O—(CH_2CH_2O)_qH \quad (II)$$

in which $R^4$ is a linear or branched aliphatic hydrocarbon radical containing 6 to 22 carbon atoms and 0, 1, 2 or 3 double bonds and q is a number of 10 to 50.

3. The process of claim/wherein in step A), component (iii) is at least one fatty acid partial glyceride of formula (III):

in which $R^5CO$ is an aliphatic acyl radical containing 6 to 22 carbon atoms.

4. The process of claim 2 wherein in step A), component (iii) is at least one fatty acid partial glyceride of formula (III):

in which $R^5CO$ is an aliphatic acyl radical containing 6 to 22 carbon atoms.

5. The process of claim 1 wherein said ratio is about (44.5 to 51.0):(16.0 to 18.0):(32.5 to 39.0).

6. The process of claim 4 wherein in step A) components (i), (ii), and (iii) are present in a ratio by weight of about (44.5 to 51.0):(16.0 to 1.0):(32.5 to 39.0).

7. The process of claim 1 wherein in step B) the alkylating agent is an alkyl halide, a dialkyl sulfate, or ethylene oxide.

8. The process of claim 1 wherein in step A) in component (i) the degree of esterification of said ester is between 1.2 and 2.5.

9. The process of claim 8 wherein in component (i) the at least one ester is derived from technical $C_{12/18}$ or $C_{16/18}$ fatty acids.

10. The process of claim 2 wherein q is a number of from 25 to 45.

11. The process of claim 10 wherein q is a number of from 30 to 40.

12. The process of claim 1 wherein in step A) component (ii) is an adduct of from 30 to 40 moles of ethylene oxide with technical $C_{12/18}$ cocoalcohol or $C_{16/18}$ tallow alcohol.

13. The process of claim 1 wherein in step A), component (iii) is at least one monoglyceride of lauric acid, palmetic acid, stearic acid, oleic acid, $C_{12/18}$ cocofatty acid, or $C_{16/18}$ tallow fatty acid.

14. In a fabric softener and conditioner or hair care formulation, the improvement wherein the esterquat prepared by the process of claim 1 is present therein.

15. The fabric softener and conditioner or hair care formulation of claim 14 wherein the esterquat is present in from about 1 0 to about 60% by weight of said formulation.

16. The solid esterquat produced by the process of claim 1.

17. The solid esterquat produced by the process of claim 2.

18. The solid esterquat produced by the process of claim 3.

19. The solid esterquat produced by the process of claim 4.

* * * * *